United States Patent
Li et al.

(10) Patent No.: US 11,521,751 B2
(45) Date of Patent: Dec. 6, 2022

(54) PATIENT DATA VISUALIZATION METHOD AND SYSTEM FOR ASSISTING DECISION MAKING IN CHRONIC DISEASES

(71) Applicant: ZHEJIANG LAB, Hangzhou (CN)

(72) Inventors: Jingsong Li, Hangzhou (CN); Shiqiang Zhu, Hangzhou (CN); Tianshu Zhou, Hangzhou (CN); Yu Tian, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 17/553,832

(22) Filed: Dec. 17, 2021

(65) Prior Publication Data

US 2022/0157468 A1    May 19, 2022

Related U.S. Application Data

(63) Continuation of application No. PCT/CN2021/073125, filed on Jan. 21, 2021.

(30) Foreign Application Priority Data

Nov. 13, 2020 (CN) .......................... 202011270972.4

(51) Int. Cl.
*G16H 50/50* (2018.01)
*G16H 10/60* (2018.01)
(Continued)

(52) U.S. Cl.
CPC .......... *G16H 50/50* (2018.01); *G06K 9/6286* (2013.01); *G06N 5/003* (2013.01); *G16H 10/60* (2018.01);
(Continued)

(58) Field of Classification Search
CPC ........ G16H 10/00–80/00; G06N 3/00–99/007; G06K 1/00; G06K 2215/111
See application file for complete search history.

(56) References Cited

U.S. PATENT DOCUMENTS

| | | | |
|---|---|---|---|
| 2008/0097938 A1* | 4/2008 | Guyon | G06N 20/00 706/12 |
| 2012/0158633 A1* | 6/2012 | Eder | G16H 50/20 707/E17.014 |

(Continued)

FOREIGN PATENT DOCUMENTS

| | | | |
|---|---|---|---|
| CA | 3009280 A1 * | 12/2018 | ........... G06F 16/288 |
| CN | 109830303 A  * | 5/2019 | |

(Continued)

OTHER PUBLICATIONS

Chen et al., "A review: Knowledge reasoning over knowledge graph," Expert Systems With Applications 141 (2020) 112948. (Year: 2020).*

(Continued)

*Primary Examiner* — Jonathon A. Szumny
(74) *Attorney, Agent, or Firm* — W&G Law Group (57) ABSTRACT

Provided is a patient data visualization method and system for assisting decision making in chronic diseases. According to the present application, a management data model diagram of a patient on a hyperplane is constructed by constructing a chronic disease knowledge graph, and combining static data and dynamic data of the patient, and then the management data model diagram is projected onto a two-dimensional plane. The difference of the Euclidean distance between features of a patient information model on a two-dimensional plane graph from the distance of standard features is compared, and a management plan is generated and recommended in combination with path node concepts and an attribute relationship between the concepts.

7 Claims, 2 Drawing Sheets

(51) Int. Cl.
*G16H 50/30* (2018.01)
*G16H 50/70* (2018.01)
*G16H 50/20* (2018.01)
*G16H 70/20* (2018.01)
*G06K 9/62* (2022.01)
*G06N 5/00* (2006.01)

(52) U.S. Cl.
CPC .......... *G16H 50/20* (2018.01); *G16H 50/30* (2018.01); *G16H 50/70* (2018.01); *G16H 70/20* (2018.01)

(56) References Cited

U.S. PATENT DOCUMENTS

| | | | |
|---|---|---|---|
| 2015/0317337 A1* | 11/2015 | Edgar | G16H 50/70 707/751 |
| 2020/0176113 A1 | 6/2020 | Megerian et al. | |
| 2021/0295822 A1* | 9/2021 | Tomkins | G06N 3/04 |

FOREIGN PATENT DOCUMENTS

| | | | |
|---|---|---|---|
| CN | 109830303 A | | 5/2019 |
| CN | 109918475 A | | 6/2019 |
| CN | 110085325 A | | 8/2019 |
| CN | 110275959 A | | 9/2019 |
| CN | 110335676 A | | 10/2019 |
| CN | 110866124 A | * | 3/2020 |
| CN | 111191048 A | | 5/2020 |
| CN | 111275486 A | | 6/2020 |
| CN | 111370127 A | | 7/2020 |
| CN | 111382272 A | | 7/2020 |
| CN | 111667894 A | | 9/2020 |
| CN | 112102937 A | | 12/2020 |
| EP | 3731239 A1 | * | 10/2020 ............... G06N 5/02 |
| WO | WO-02103954 A2 | * | 12/2002 ............... G06K 9/623 |
| WO | WO-2020139861 A1 | * | 7/2020 ............ G06F 16/367 |

OTHER PUBLICATIONS

Razzak et al., "Big data analytics for preventive medicine," Neural Computing and Applications (2020) 32:4417-4451. (Year: 2020).*
Wang et al., "Knowledge Graph Embedding by Translating on Hyperplanes," Proceedings of the Twenty-Eighth AAAI Conference on Artificial Intelligence. (Year: 2014).*
Lin et al., "Patient Similarity via Joint Embeddings of Medical Knowledge Graph and Medical Entity Descriptions," Special Section On Emerging Deep Learning Theories and Methods for Biomedical Engineering vol. 9, 2020, pp. 156663-156676. (Year: 2020).*
Nicholson et al., "Constructing knowledge graphs and their biomedical applications," Computational and Structural Biotechnology Journal 18 (2020) 1414-1428. (Year: 2020).*
Chen et al., "A review: Knowledge reasoning over knowledge graph," Expert Systems With Applications 141 (2020) 112948; https://doi.org/10.1016/j.eswa.2019.112948. (Year: 2020).*
International Search Report (PCT/CN2021/073125); dated Apr. 23, 2021.
First Office Action(202011270972.4); dated Dec. 28, 2020.
Notice Of Allowance(202011270972.4); dated Jan. 15, 2021.
Personalized Health Knowledge Graph; dated Oct. 31, 2018.
Research on Smart Decision-Making Method for Upper Gastrointestinal Diseases Based on Electronic Gastroscopic Video; dated Nov. 30, 2019.
Research on Smart Decision-Making Method for Upper Gastrointestinal Diseases Based on Electronic Gastroscopic Video; Date of Mailing: Nov. 30, 2019.

* cited by examiner

PATIENT DATA VISUALIZATION METHOD AND SYSTEM FOR ASSISTING DECISION MAKING IN CHRONIC DISEASES

CROSS-REFERENCE TO RELATED APPLICATIONS

The present application is a continuation of International Application No. PCT/CN2021/073125, filed on Jan. 21, 2021, which claims priority to Chinese Application No. 202011270972.4, filed on Nov. 13, 2020, the contents of both of which are incorporated herein by reference in their entireties.

TECHNICAL FIELD

The present application belongs to the technical field of visualization of medical treatment and data, and in particular relates to a patient data visualization method and system for assisting decision making in chronic diseases.

BACKGROUND

Chronic diseases, also known as chronic non-communicable diseases, mainly include cardiovascular and cerebrovascular diseases (hypertension, coronary heart disease, stroke), diabetes, chronic respiratory diseases, and so on, and have the characteristics that the onset is hidden, the course of the disease is long, the condition is protracted, the cause of the disease is complex, and some have not been fully confirmed. With the rapid economic development in China and the changes in the lifestyles of people, the number of patients with chronic diseases and deaths has continued to increase, and the burden of disease on people has become heavier. The chronic diseases have become one of the major public health problems that seriously threaten the health of our residents and affect the national economic and social development. Data shows that domestic chronic diseases account for about 86% of disease mortality and 76% of the burden of disease. The chronic diseases are difficult to cure, and mainly rely on the long-term self-health management of the patients. For electronic medical record information and data recorded in daily management, such as diets, exercises and daily physical sign data of the patients, certain analysis is performed to provide a data visualization method for assisting decision making, which is beneficial for the patients to understand their own health conditions and adjust health management plans in time, and is also beneficial for doctors to formulate and recommend management plans for the patients, thereby saving medical resources. The visualization manner can clearly show patient management goals and provide precise health-related helps, thereby enhancing the compliance of patient management.

The existing chronic disease data visualization technology mainly refers to that data recorded in the daily management of the patients are presented in an application program in the form of data charts. The more commonly used data design components are histograms, line charts, circular charts, and the like, which are simple and easy to understand, and thus are accepted by users easily. The patients realize the effects of zooming in, zooming out, rotating, and shifting pictures on mobile terminals through the multi-touch technology. Auxiliary decision making support visualization is mainly displayed in the form of importance ranking, correlation matrix, and the like, it is not a user-friendly visualization solution, and meanwhile, information transmission is not comprehensive and rich enough; and the shortcomings of the existing chronic disease data visualization solutions are as follows:

(1) only daily physical signs and other data recorded by the patients on the mobile terminals are displayed to express a certain trend, which lacks evaluation systems of daily management effects of the patients, such that the patients and medical staff cannot clarify the effects of health management of the patients on their health conditions.

(2) Most of the data are represented in basic graphs such as line charts and histograms, which cannot reflect the association between chronic disease risk factors, and various types of data are separately counted and plotted, and thus cannot systematically and comprehensively integrate multi-dimensional information of the patients, and semantic information such as the relevance and importance of the chronic disease risk factors of the patients.

(3) Various types of data such as personal physical conditions, exercise and diet habits of the patients are not comprehensively considered in the health management plans, therefore, the decision making lacks individualization, and patient data are not fully used when the contents of the management plans are formulated and recommended.

SUMMARY

On the basis of electronic medical record data and various daily recorded data (exercises, diets, physical signs, medication, assays and the like) of patients, and in combination with semantic technology, clinical decision making support technology and visualization technology, the present application proposes a patient data visualization method and system for assisting decision making in chronic diseases.

In the present application, a management data model diagram of a patient on a hyperplane is constructed by constructing a chronic disease knowledge graph, and combining static data and dynamic data of the patient, and then the management data model diagram is projected onto a two-dimensional plane. The difference of an Euclidean distance between features of a patient information model on a two-dimensional plane graph from the distance of standard features is compared (a two-dimensional plane mapping graph of the patient with a good management effect diagnosed by a doctor), and a management plan is generated and recommended in combination with path node concepts and an attribute relationship between the concepts. By fusing the patient information model with the chronic disease knowledge graph, the semantic information of each feature can be fully utilized to comprehensively and systematically display the importance and association of various risk factors on the two-dimensional plane in the form of positions, colors and the like. The chronic disease management effect of the patient is evaluated through a geometric position, and then a personalized health management plan is formulated for the patient by using paths, so as to help the patient improve the chronic disease management capability from multiple dimensions.

According to the patient data visualization method for assisting decision making in chronic diseases proposed in the present application, the specific implementation of the method includes the following steps:

(1) constructing a chronic disease knowledge graph: receiving clinical guidelines and knowledge literature related to chronic diseases as knowledge sources of the knowledge graph, performing unique identification on data semantics through Systematized Nomenclature of Medicine Clincal Terms (SNOMED CT), manually constructing categories, attributes and instances, adding a data relationship and an attribute relationship, and generating a knowledge graph prototype file;

(2) establishing a patient information model: collecting patient information; performing Resource Description Framework (RDF) conversion on patient data, so as to convert data in a patient database into an RDF triple relationship that meets the Web Ontology Language (OWL) language specification; identifying nodes of the patient information model by using SNOMED CT, so as to achieve semantic extension of the patient data to domain knowledge, and fusing the patient information with the chronic disease knowledge graph to construct the patient information model;

(3) drawing a hyperplane feature map: converting the patient information model into the hyperplane feature map through a distributed representation, wherein the distributed representation adopts a translation-based model between entity vectors and relationship vectors;

(4) mapping a two-dimensional plane: the position information of a two-dimensional plane node corresponding to a two-dimensional position of the hyperplane feature map of the patient information model after dimensionality reduction, distinguishing different information categories in the knowledge graph by using the colors of the nodes, using a feature importance ranking of the Regularized Gradient Boosted Decision Tree algorithm as the ranking of correlation between each node and disease progression, and using a feature weight value as a calculation weight of the Euclidean distance; and (5) decision making support feedback: taking a domain expert marking result as the standard for the patient information model with an ideal chronic disease management effect, drawing a two-dimensional plane mapping image of the patient data through distributed representation and dimensionality reduction visualization, and calculating the Euclidean distance between geometric centers of various feature areas in the mapping image in combination with the feature weight value to serve as a standardized management target; calculating the Euclidean distance between the features of a patient who requires decision making support feedback in the two-dimensional plane mapping image, and comparing the Euclidean distance with a standard numerical value in combination with the feature weight value calculated from the Euclidean distance, so as to find a path of similar distance; and obtaining knowledge in the knowledge graph according to the distance information of the features.

Further, the knowledge content of the knowledge graph covers disease diagnosis, inspection items, physical sign states, related diseases, therapeutic drugs, living habits, measurement units, and detection quantities.

Further, the patient information collected in step (2) includes patient health data manually input in a daily mobile terminal or collected by a wearable device, and patient electronic medical record data recorded by a regional chronic disease management center.

Further, during the RDF conversion process of the patient data in step (2), the data in a relational database are mapped into a RDF format by using the Database to RDF (D2R) semantic mapping technology; D2R includes a D2R Server, a D2RQ (D2RQ is Open Source software and published under the Apache license. The source code is available on GitHub. A D2RQ Platform is a system for accessing relational databases as virtual, read-only RDF graphs. It offers RDF-based access to the content of relational databases without having to replicate it into an RDF store.) Engine and a D2RQ Mapping language; the D2RQ Mapping language defines Mapping rules for converting the relational data into the RDF format; and the D2RQ Engine uses a customized D2RQ Mapping file to complete data mapping, which specifically refers to mapping tables and fields in the relational database into categories and attributes in Web Ontology Language (OWL) file respectively, and obtaining the relationship between the categories from a table that expresses the relationship.

Further, drawing the hyperplane feature map in step (3) specifically includes the following sub-steps:

(3.1) encoding triples into spatial distributed vectors by using a translating on hyperplanes (TransH) model, specifically:

the knowledge in the patient information model is stored in the form of a triple (h, r, t), wherein h represents a head entity vector, r represents a relationship vector, and t represents a tail entity vector; sets of triples form a directed graph, graph nodes represent entities, edges represent different types of relationships, and the edges are directed to indicate that the relationships are asymmetric; entity distributed vectors of reflexive relationship, many-to-one, one-to-many and many-to-many relationships are constructed by means of the TransH model;

(3.2) optimizing an objective function, specifically:

for each relationship r in the TransH model, it is assumed that there is a corresponding hyperplane, a relationship projection of r on the hyperplane is expressed as $d_r$, a normal vector of the hyperplane is expressed as and $\omega_r$, and $\|\omega_r\|_2=1$, $h_\perp$ and $t_\perp$ respectively represent projections of h and t on the hyperplane, then:

$$h_\perp = h - \omega_r^T h \omega_r,\ t_\perp = t - \omega_r^T t \omega_r$$

defining a scoring function as:

$$f_r(h,t) = \|h_\perp + d_r - t_\perp\|_2^2$$

to obtain the objective function:

$$L = \sum_{(h,r,t)\in S} \sum_{(h',r,t')\in S'} [\varepsilon + f_r(h,t) - f_r(h',t')]_+$$

where, S represents a triple in a knowledge base, S' represents a triple of negative sampling, and ε represents an interval distance parameter with a value greater than 0; and during the process of optimizing the objective function L, it is necessary to specify that the value of a positive example triple is small and the value of a negative example triple is large, that is, the ranking loss is minimized; and after the training of the TransH model is completed by using a stochastic gradient descent training method, vector representations of the entities and the relationships are obtained.

Further, the step (4) of mapping the two-dimensional plane specifically includes the following sub-steps:

(4.1) using the t-distributed Stochastic Neighbor Embedding (t-SNE) algorithm to perform dimensionality reduction visualization, specifically:

step 1: assuming that a data set X has a total of N data points, and the dimension of each data point $x_i$ is D, reducing the dimensions to two dimensions, that is, expressing all data on the plane;

calculating a conditional probability of similarity between the data points in a high-dimensional space; converting the high-dimensional Euclidean distance between the data points into the conditional probability representative of similarity, wherein the conditional probability $P_{j|i}$ of similarity between high-dimensional data points $x_i$ and $x_j$ is as follows:

$$P_{j|i} = \frac{\exp(-\|x_i - x_j\|^2 / 2\sigma_i^2)}{\sum_{k \neq i} \exp(-\|x_i - x_k\|^2 / 2\sigma_i^2)}$$

where, $\sigma_i$ represents the Gaussian variance centered on the data point $x_i$;

step ii: calculating the conditional probability of similarity between the data points in a low-dimensional space, wherein for low-dimensional corresponding points $y_i$ and $y_j$ of the high-dimensional data points $x_i$ and $x_j$, the conditional probability is calculated as follows:

$$Q_{j|i} = \frac{\exp(-\|y_i - y_j\|^2)}{\sum_{k \neq i} \exp(-\|y_i - y_k\|^2)}$$

step iii: minimizing a difference in the conditional probabilities, that is, making the conditional probability $Q_{j|i}$ approximate to $P_{j|i}$; it is achieved by minimizing the Kullback-Leibler divergence between the two conditional probability distributions, and performing iterative updating by using gradient descent, and a loss function is as follows:

$$C = \sum_i KL(P_i \| Q_i) = \sum_i \sum_j P_{j|i} \log \frac{P_{j|i}}{Q_{j|i}}$$

(4.2) feature importance ranking: using the Regularized Gradient Boosted Decision Tree algorithm to achieve the importance ranking of each entity in the knowledge graph and to obtain the feature weight value, specifically:

the data set is a patient information model with known chronic disease management effects or outcomes, each sample contains n-dimensional features (the number of entities in the patient information model); the objective function L of the Regularized Gradient Boosted Decision Tree includes a loss function and complexity, which are defined as:

$$L = \sum_i l(\hat{y}_i, y_i) + \sum_k \Omega(f_k)$$

$$\Omega(f_k) = \gamma T + \frac{1}{2}\lambda \sum_{j=1}^{T} \omega_j^2$$

where i represents an $i^{th}$ sample, k represents a $k^{th}$ tree, $\hat{y}_i$ represents a predicted output, $y_i$ represents a label value, T represents the number of leaf nodes, and $\omega$ represents a leaf weight value; $\gamma$ represents a leaf tree penalty regular term, which has a function of pruning; $\lambda$ represents a leaf weight penalty regular term, which prevents over-fitting; $l(\hat{y}_i, y_i)$ represents a prediction error of the $i^{th}$ sample; $\Sigma_i l(\hat{y}_i, y_i)$ represents the loss function; $\Sigma_k \Omega(f_k)$ represents the complexity function of a tree;

during the growth of the tree, by comparing the values of the objective function before and after splitting, the splitting with the minimum value of the objective function after the splitting is an optimal splitting point $$Gain = \frac{1}{2}\left[\frac{G_L^2}{H_L + \delta} + \frac{G_R^2}{H_R + \delta} - \frac{(G_L + G_R)^2}{H_L + H_R + \delta}\right] - \delta$$

where $\delta$ represents a complexity cost introduced by adding a new leaf node, $G_L$ represents a left sub-tree gradient value, and $H_L$ represents is a second derivative of a left sub-tree sample set; $G_R$ represents a right sub-tree gradient value, and $H_R$ represents the second derivative of a right sub-tree sample set; if Gain<0, then this leaf node will not be split; and a feature importance score is realized by calculating a total gain brought by a certain feature in all trees every time when the node is split; and the corresponding feature weight value is obtained by calling a get_score method of a booster parameter.

Further, during the feature importance ranking process in step (4), the Regularized Gradient Boosted Decision Tree parameter training is performed by using a grid search method, including a general parameter, an improving parameter, and a learning target parameter; and the general parameter controls macro parameters, the improving parameter controls the improvement in each step, and the learning target parameter controls the performance of a training target.

Further, in step (5), the knowledge in the knowledge graph is obtained according to the distance information of the features by using a SPARQL Protocol and RDF Query Language (SPARQL) query language and Jena rule reasoning, so as to generate a personalized management plan for the patient.

Further, in step (5), a SPARQL query statement includes conditions to which query information and names should conform, the conditions appear in a form of triples and are arranged in the order of <subject, predicate, object>, that is, subject, predicate, and object, and a query result is actually a matching result of the condition triples and a RDF triples in the data file.

A patient data visualization system for assisting decision making in chronic diseases proposed in the present application includes the following modules:

a chronic disease knowledge graph construction module: with clinical guidelines and knowledge literature related to chronic diseases as knowledge sources of a knowledge graph, performing unique identification on data semantics through SNOMED CT, manually constructing categories, attributes and instances, adding a data relationship and an attribute relationship, and generating a knowledge graph prototype file;

a patient information model construction module: collecting patient information, and converting data in a patient database into an RDF triple relationship that meets the OWL language specification; identifying nodes of a patient information model by using SNOMED CT, so as to achieve semantic extension of the patient data to domain knowledge, and fusing the patient information with the chronic disease knowledge graph to construct the patient information model;

a hyperplane feature map drawing module: converting the patient information model into a hyperplane feature map through a distributed representation, wherein the distributed representation adopts a translation-based model between entity vectors and relationship vectors;

a two-dimensional plane mapping module: the position information of a two-dimensional plane node corresponding to a two-dimensional position of the hyperplane feature map of the patient information model after dimensionality reduction, distinguishing different information categories in the knowledge graph by using the colors of the nodes, using a feature importance ranking of the Regularized Gradient Boosted Decision Tree algorithm as the ranking of correlation between each node and disease progression, and using a feature weight value as a calculation weight of the Euclidean distance; and a decision making support feedback module: taking a domain expert marking result as the standard for the patient information model with an ideal chronic disease management effect, drawing a two-dimensional plane mapping image of the patient data through distributed representation and dimensionality reduction visualization, and calculating the Euclidean distance between geometric centers of various feature areas in the mapping image in combination with the feature weight value to serve as a standardized management target; calculating the Euclidean distance between the features of a patient who requires decision making support feedback in the two-dimensional plane mapping image, and comparing the Euclidean distance with a standard numerical value in combination with the feature weight value calculated from the Euclidean distance, so as to find a path of similar distance; and obtaining knowledge in the knowledge graph according to the distance information of the features.

The beneficial effect of the present application is that compared with the existing visualization solutions for chronic disease data, the present application can visually construct two-dimensional plane mapping images of various types of patient data in combination with the knowledge graph, and it is a user-friendly visualization solution. The relevance, features and importance of the patient information can be expressed by means of distances and colors of the nodes on the two-dimensional plane, so that comprehensive and rich information can be conveyed. The chronic disease management effect of the patient is evaluated through the geometric position, and then a personalized health management plan is formulated for the patient by using paths, so as to help the patient improve the chronic disease management capability from multiple dimensions, which is conducive to improving the patient compliance. The present application realizes long-term continuous, cyclical and spiral-increasing whole-process all-around visual health management service from health information collection, health evaluation to health promotion.

DESCRIPTION OF EMBODIMENTS

In order to make the above-mentioned objectives, features and advantages of the present application more obvious and understandable, the specific embodiments of the present application will be described in detail below with reference to the drawings.

In the following description, many specific details are set forth in order to fully understand the present application, but the present application can also be implemented in other ways different from those described here, and those skilled in the art can make similar promotion without departing from the connotation of the present application, therefore, the present application is not limited by the specific embodiments disclosed below.

Figure 1:
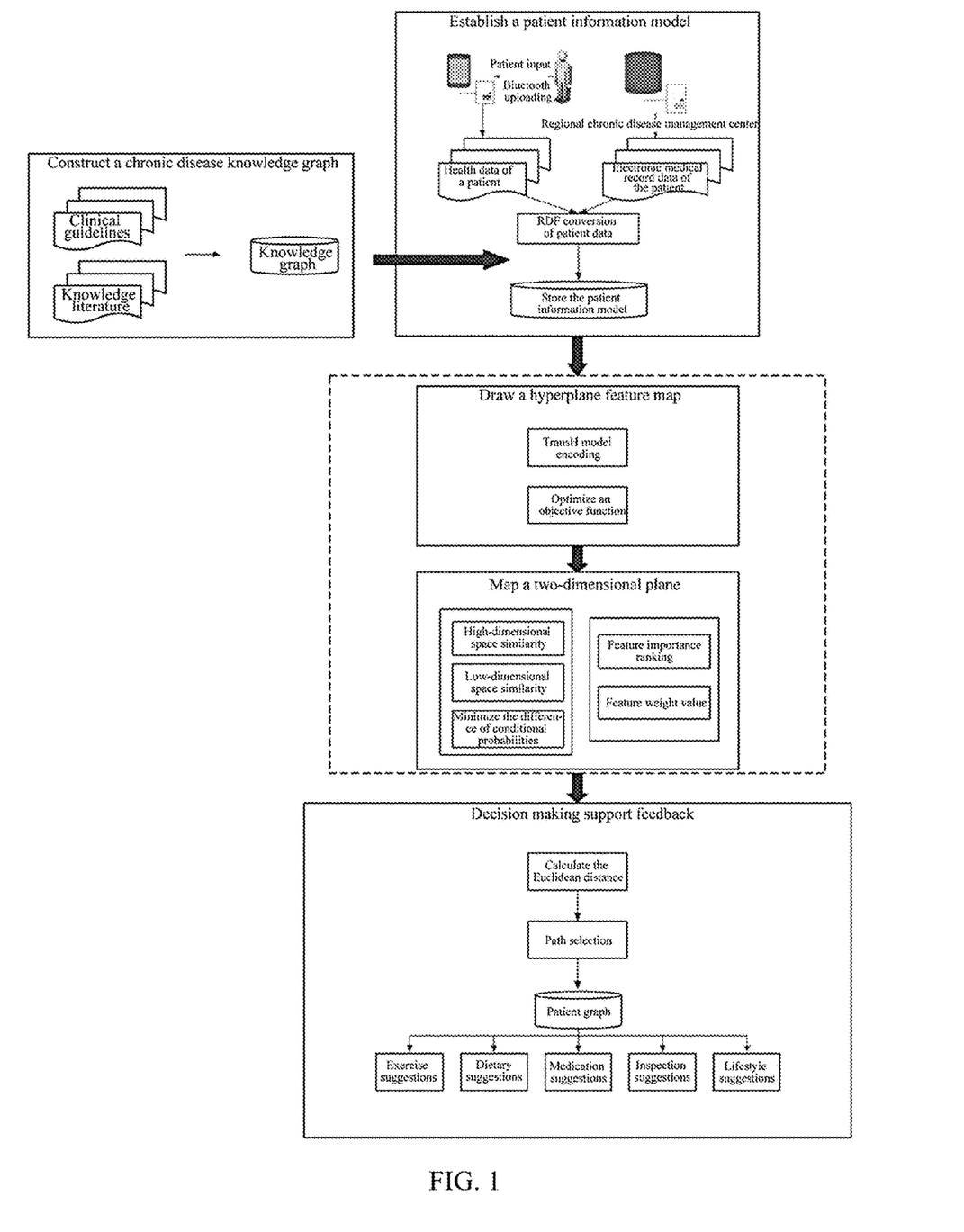
FIG. 1 is a flowchart of implementing a patient data visualization method for assisting decision making in chronic diseases according to the present application.

The present application proposes a patient data visualization method and system for assisting decision making in chronic diseases, which can help a patient to better understand personal health conditions and disease intervention conditions, and help a doctor more efficiently view the conditions of the patient and formulate a health management plan. As shown in FIG. 1, the specific implementation of the method of the present application includes the following steps:

(1) Constructing a Chronic Disease Knowledge Graph

Clinical guidelines and knowledge literature related to chronic diseases are used as knowledge sources of the knowledge graph, the knowledge content covers disease diagnosis, inspection items, physical signs, related diseases, treatment drugs, living habits, and the like, and also includes medical auxiliary words such as measurement units and detection quantities. The SNOMED CT is selected as a standardized encoding system, unique identification is performed on data semantics through SNOMED CT, categories, attributes, instances and other information are manually constructed, a data relationship and an attribute relationship are added, and a knowledge graph prototype file is generated.

(2) Establishing a Patient Information Model (2.1) Collecting Patient Information There are two main sources of patient information: one type is patient health data manually input in a daily mobile terminal or collected by a wearable device; and the other type is patient electronic medical record data recorded by a regional chronic disease management center.

(2.2) RDF Conversion of Patient Data

Data in the formats of Extensible Markup Language (XML), JavaScript Object Notation (JSON) and the like in a patient database need to be converted into RDF (Resource Description Framework) triple relationships that conform to the OWL language specification. Herein, the data in a relational database are mapped into the RDF format by using the D2R semantic mapping technology. D2R mainly includes a D2R Server, a D2RQ Engine and a D2RQ Mapping language. The D2RQ Mapping language defines Mapping rules for converting the relational data into in the RDF format. The D2RQ Engine uses a customized D2RQ Mapping file to complete data mapping, which specifically refers to mapping tables and fields in the relational database into categories and attributes in an OWL file respectively, and obtaining the relationship between the categories from a table that expresses the relationship. Like the chronic disease knowledge graph, the SNOMED CT is used for identifying nodes of the patient data model, thereby realizing the semantic extension of the patient data to domain knowledge, and the patient information is fused with the chronic disease knowledge graph to construct the patient information model.

(3) Drawing a Hyperplane Feature Map

The patient information model is converted into the hyperplane feature map through a distributed representation, and the distributed representation adopts a translation-based model between entity vectors and relationship vectors.

Figure 2:
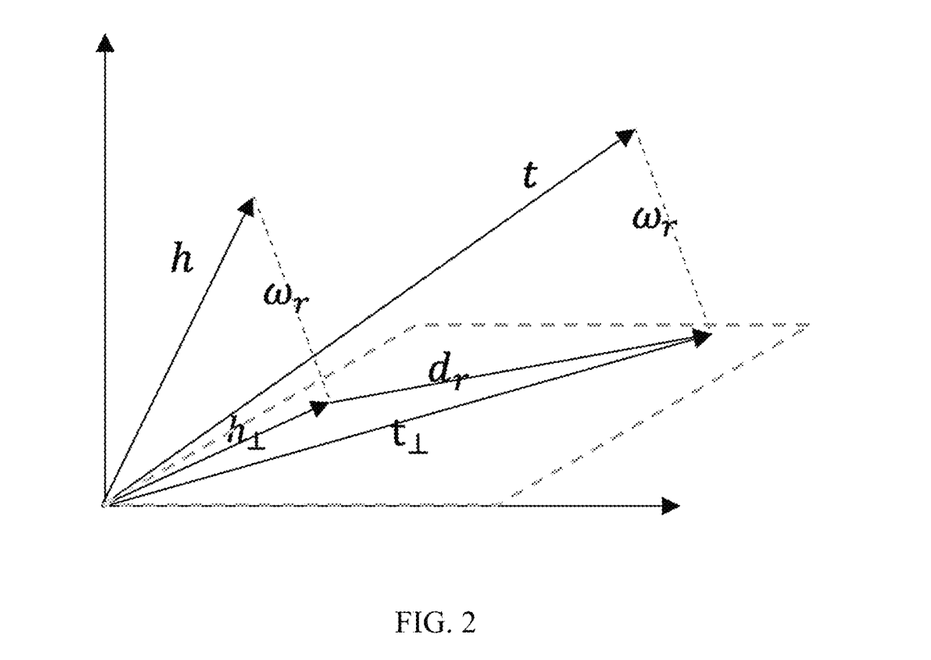
FIG. 2 is a schematic diagram of a TransH model.

Step i: encoding triples into spatial distributed vectors by using a TransH model, as shown in FIG. 2.

The TransH replaces head and tail entities with different probabilities according to the type of the relationship r (one-to-one, one-to-many, many-to-one, and many-to-many). For example, for the one-to-many relationship, replacing the head entity is more likely to obtain a legal negative sample than replacing the tail entity, so the head entity can be replaced with a greater probability. For the triple corresponding to the relationship r, the TransH first counts the number of tail entities tph corresponding to each head entity on average and the number of head entities hpt corresponding to each tail entity on average, and then defines a Bernoulli distribution to replace the head entity with a probability $$\frac{tph}{tph+hpt},$$

and to replace the tail entity with a probability $$\frac{hpt}{tph+hpt}.$$

The knowledge in the patient information model is stored in the form of a triple (h, r, t), wherein h represents a head entity vector, and r represents a relationship vector, and t represents a tail entity vector. Sets of triples form a directed graph, graph nodes represent entities, edges represent different types of relationships, and the edges are directed to indicate that the relationships are asymmetric. Entity distributed vectors of reflexive relationship, many-to-one, one-to-many and many-to-many relationships can be constructed by means of the TransH model.

Step ii: optimizing an objective function. For each relationship r in the TransH model, it is assumed that there is a corresponding hyperplane (the relationship r falls in the hyperplane), a relationship projection of r on the hyperplane is expressed as $d_r$, a normal vector of the hyperplane is expressed as $\omega_r$, and $\|\omega_r\|_2=1$, $h_{195}$ and $t_\perp$ respectively represent projections of h and t on the hyperplane, then:

$$h_\perp = h - \omega_r^T h \omega_r, \quad t_\perp = t - \omega_r^T t \omega_r$$

defining a scoring function as:

$$f_r(h,t) = \|h_\perp + d_r - t_\perp\|_2^2$$

to obtain the objective function:

$$L = \sum_{(h,r,t)\in S} \sum_{(h',r,t')\in S'} [\varepsilon + f_r(h,t) - f_r(h',t')]_+$$

where, S represents a triple in a knowledge base, S' represents a triple of negative sampling, and ε represents an interval distance parameter with a value greater than 0, and is a hyperparameter, $[x]_+$ represents a positive value function, that is, when x>0, $[x]_+=x$, and when X ≤0, $[x]_+=0$. if the value of the scoring function value of the two nodes is relatively low, it means that the distance is relatively small, and vice versa. During the process of optimizing the objective function, it is necessary to specify that the value of a positive example triple is small and the value of a negative example triple is large, that is, the ranking loss is minimized. After the training of the TransH model is completed by using a Stochastic Gradient Descent (SGD) training method, vector representations of the entities and the relationships can be obtained.

Figure 3:
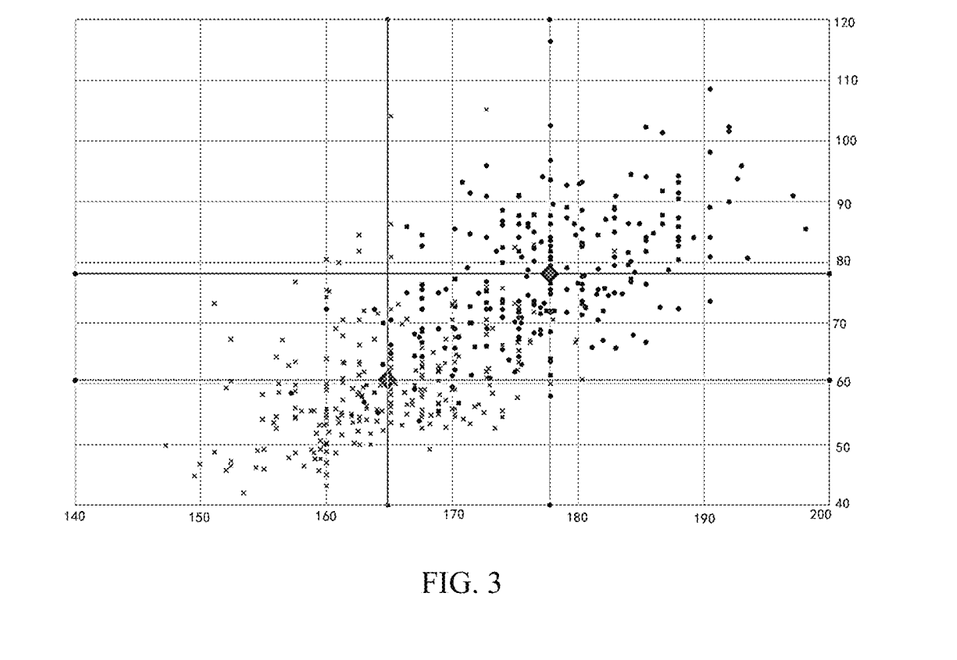
FIG. 3 is a schematic diagram of mapping a two-dimensional plane.

(4) Mapping a Two-Dimensional Plane

The position information of a two-dimensional plane node corresponds to a two-dimensional position of the hyperplane feature map of the patient information model after dimensionality reduction, different information categories in the knowledge graph are distinguished by using the colors of the nodes, a feature importance ranking of the Regularized Gradient Boosted Decision Tree algorithm is used as the ranking of correlation between each node and disease progression, and a feature weight value is used as a calculation weight of the Euclidean distance.

(4.1) Dimensionality Reduction Visualization

Dimensionality reduction visualization is performed by using the t-SNE algorithm.

The t-SNE algorithm is a machine learning method for dimensionality reduction, which can help us identify associated patterns. The main advantage of t-SNE is the ability to maintain a local structure. This means that the projections of points with close distances in a high-dimensional data space are still close to each other after being projected into a low-dimensional data space. The t-SNE can also generate beautiful visualization.

The t-SNE algorithm models the distribution of the neighbors of each data point, wherein the neighbor refers to a set of data points close to each other. In the original high-dimensional space, we model the high-dimensional space as a Gaussian distribution, and in a two-dimensional output space, we can model it as a t-distribution. The goal of this process is to find a transformation of mapping the high-dimensional space into a two-dimensional space, and to minimize the gap of all points between the two distributions. Compared with the Gaussian distribution, the t distribution has a longer tail, which is beneficial for more uniform distribution of the data points in the two-dimensional space.

Step i: assuming that a data set X has a total of N data points, and the dimension of each data point $x_i$ is D, reducing the dimensions to d dimensions, wherein d is taken as 2 here, that is, expressing all data on the plane; calculating a conditional probability of similarity between the data points in the high-dimensional space; converting the high-dimensional Euclidean distance between the data points into the conditional probability representative of similarity, wherein the conditional probability $P_{j|i}$ of similarity between high-dimensional data points $x_i$ and $x_j$ is as follows:

$$P_{j|i} = \frac{\exp(-\|x_i - x_j\|^2 / 2\sigma_i^2)}{\sum_{k \neq i} \exp(-\|x_i - x_k\|^2 / 2\sigma_i^2)}$$

where, $\sigma_i$ represents the Gaussian variance centered on the data point $x_i$.

Step ii: calculating the conditional probability of similarity between the data points in the low-dimensional space; and for low-dimensional corresponding points $y_i$ and $y_j$ of the high-dimensional data points $x_i$ and $x_j$, the conditional probability $Q_{j|i}$ is calculated as follows:

$$Q_{j|i} = \frac{\exp(-\|y_i - y_j\|^2)}{\sum_{k \neq i} \exp(-\|y_i - y_k\|^2)}$$

Step iii: minimizing a difference in the conditional probabilities, that is, making the conditional probability $Q_{j|i}$ approximate to $P_{j|i}$. This step is achieved by minimizing the Kullback-Leibler divergence (KL divergence) between the two conditional probability distributions. Iterative updating is performed in this process by using gradient descent, and a loss function is as follows, that is, the loss function is minimized:

$$C = \sum_i KL(P_i \| Q_i) = \sum_i \sum_j P_{j|i} \log \frac{P_{j|i}}{Q_{j|i}}$$

The schematic diagram of mapping the two-dimensional plane is shown in FIG. 3. The figure shows projection points of various entities of two different types of features, which correspond to approximate projection areas of such features, and the center point of each type of features is marked. The distance between the center points and the clustering conditions of the projection points can determine the correlation between the features.

(4.2) Feature Importance Ranking

The Regularized Gradient Boosted Decision Tree algorithm (eXtreme Gradient Boosting, extreme gradient boosting algorithm) is used to achieve the importance ranking of each entity in the knowledge graph and to obtain the feature weight value. The data set is a patient information model with known chronic disease management effects or outcomes, each sample contains n-dimensional features (the number of entities in the patient information model). The objective function L of the Regularized Gradient Boosted Decision Tree includes a loss function and complexity, which are defined as:

$$L = \sum_i l(\hat{y}_i, y_i) + \sum_k \Omega(f_k)$$

$$\Omega(f_k) = \gamma T + \frac{1}{2}\lambda \sum_{j=1}^{T} \omega_j^2$$

where i represents the $i^{th}$ sample, k represents the $k^{th}$ tree, $\hat{y}_i$ represents a predicted output, $y_i$ represents a label value, T represents the number of leaf nodes, and ω represents a leaf weight value; γ represents a leaf tree penalty regular term, which has a function of pruning; λ represents a leaf weight penalty regular term, which prevents over-fitting; $l(\hat{y}_i, y_i)$ represents a prediction error of the $i^{th}$ sample, and the smaller the error value, the better; $\Sigma_i l(\hat{y}_i, y_i)$ represents the loss function; $\Sigma_k \Omega(f_k)$ represents the complexity function of the tree, and the lower the complexity is, the stronger the generalization ability of the model is.

During the growth of the tree, by comparing the values of the objective function before and after splitting, the splitting with the minimum value of the objective function after the splitting is an optimal splitting point. The Gain here can be regarded as subtracting left and right objective function values after splitting from the objective function value before splitting, therefore if Gain<0, this leaf node will not be split. δ represents a complexity cost introduced by adding a new leaf node, $G_L$ represents a left sub-tree gradient value, and $H_L$ represents is a second derivative of a left sub-tree sample set; $G_R$ represents a right sub-tree gradient value, and $H_R$ represents the second derivative of a right sub-tree sample set; and $$\frac{G_L^2}{H_L + \delta}$$

can evaluate the structure of a tree.

$$\text{Gain} = \frac{1}{2}\left[\frac{G_L^2}{H_L + \delta} + \frac{G_R^2}{H_R + \delta} - \frac{(G_L + G_R)^2}{H_L + H_R + \delta}\right] - \delta$$

A feature importance score is realized by calculating a total gain, that is, total gain, brought by a certain feature in all trees every time when the node is split. The score evaluate the value of the feature in improving the construction of the decision making tree, and thus can be used as an indicator of feature importance ranking. Finally, a corresponding feature weight value is obtained by calling a get_score method of a booster parameter.

In this step, the Regularized Gradient Boosted Decision Tree parameter training is performed by using a grid search method, including a general parameter, an improving parameter, and a learning target parameter; and the general parameter controls macro parameters, the improving parameter controls the improvement in each step, and the learning target parameter controls the performance of a training target.

(5) Decision Making Support Feedback

A domain expert marking result is taken as the standard for the patient information model with an ideal chronic disease management effect, a two-dimensional plane mapping image of the patient data is drawn through distributed representation and dimensionality reduction visualization, and the Euclidean distance between geometric centers of various feature areas in the mapping image is calculated in combination with the feature weight value to serve as a standardized management target. The Euclidean distance between the features of a patient who requires decision making support feedback in the two-dimensional plane mapping image is calculated, and the Euclidean distance is compared with a standard numerical value in combination with the feature weight value calculated from the Euclidean distance, so as to find a path of similar distance. Knowledge in the knowledge graph is obtained according to the distance information of the features by using SPARQL query language and Jena rule reasoning, and a personalized management plan is generated for the patient, including exercise suggestions, dietary suggestions, medication suggestions, inspection suggestions, lifestyle suggestions, and the like. The SPARQL query statement includes conditions to which query information and names should conform, the conditions appear in the form of triples and are arranged in the order of <subject, predicate, object>, that is, subject, predicate, and object, the query condition becomes a pattern, and the query result is actually a matching result of the condition triples and the RDF triples in the data file. The Jena reasoning is based on rules, and the rules are defined by Rule objects.

The present application further provides a patient data visualization system for assisting decision making in chronic diseases, including the following modules:

a chronic disease knowledge graph construction module: with clinical guidelines and knowledge literature related to chronic diseases as knowledge sources of a knowledge graph, performing unique identification on data semantics through SNOMED CT, manually constructing categories, attributes and instances, adding a data relationship and an attribute relationship, and generating a knowledge graph prototype file;

a patient information model construction module: collecting patient information, and converting data in a patient database into an RDF triple relationship that meets the OWL language specification; identifying nodes of a patient information model by using SNOMED CT, so as to achieve semantic extension of the patient data to domain knowledge, and fusing the patient information with the chronic disease knowledge graph to construct the patient information model;

a hyperplane feature map drawing module: converting the patient information model into a hyperplane feature map through a distributed representation, wherein the distributed representation adopts a translation-based model between entity vectors and relationship vectors;

a two-dimensional plane mapping module: the position information of a two-dimensional plane node corresponding to a two-dimensional position of the hyperplane feature map of the patient information model after dimensionality reduction, distinguishing different information categories in the knowledge graph by using the colors of the nodes, using a feature importance ranking of the Regularized Gradient Boosted Decision Tree algorithm as the ranking of correlation between each node and disease progression, and using a feature weight value as a calculation weight of the Euclidean distance; and a decision making support feedback module: taking a domain expert marking result as the standard for the patient information model with an ideal chronic disease management effect, drawing a two-dimensional plane mapping image of the patient data through distributed representation and dimensionality reduction visualization, and calculating the Euclidean distance between geometric centers of various feature areas in the mapping image in combination with the feature weight value to serve as a standardized management target; calculating the Euclidean distance between the features of a patient who requires decision making support feedback in the two-dimensional plane mapping image, and comparing the Euclidean distance with a standard numerical value in combination with the feature weight value calculated from the Euclidean distance, so as to find a path of similar distance; and obtaining knowledge in the knowledge graph according to the distance information of the features.

The above descriptions are only preferred embodiments of the present application. Although the present application has been disclosed as above by the preferred embodiments, the present application is not limited thereto. Anyone familiar with this art, without departing from the scope of the technical solutions of the present application, can use the method and technical content disclosed above to make many possible changes and modifications to the technical solutions of the present application, or modify the technical solutions into equivalent embodiments of equivalent changes. For example, feature importance ranking can also use the Categorical Boosting (CatBoost) algorithm, and the Light GBM algorithm. Distributed representation can also use translation models such as, Translating on Generative Mixture Model (TransG), Translating on Relation Space (TransR) and Cluster Translating on Relation Space (CTransR). The mapping of the two-dimensional plane can also use Principal Component Analysis (PCA), Sammon mapping, SNE and other dimensionality reduction algorithms. Therefore, any simple changes, equivalent changes and modifications made to the above embodiments based on the technical essence of the present application, without departing from the content of the technical solutions of the present application, still fall within the protection scope of the technical solutions of the present application.

What is claimed is:
1. A patient data visualization method for assisting decision making in chronic diseases, comprising the following steps:

(1) constructing a chronic disease knowledge graph: receiving clinical guidelines and knowledge literature related to chronic diseases as knowledge sources of the chronic disease knowledge graph, performing unique identification on data semantics through Systematized Nomenclature of Medicine Clincal Terms (SNOMED CT), manually constructing categories, attributes and instances, adding a data relationship and an attribute relationship, and generating a knowledge graph prototype file;

(2) establishing a patient information model: collecting patient data; performing Resource Description Framework (RDF) conversion on the patient data, so as to convert the patient data in a patient database into an RDF triple relationship that conforms to a Web Ontology Language (OWL) language specification by using a Database to RDF (D2R) semantic mapping technology to map the patient data in a relational database into a RDF format; identifying nodes of the patient information model by using SNOMED CT, so as to achieve semantic extension of the patient data to domain knowledge, and fusing the patient data with the chronic disease knowledge graph to construct the patient information model;

(3) drawing a hyperplane feature map: converting the patient information model into the hyperplane feature map through a distributed representation, wherein the distributed representation adopts a translation-based model between entity vectors and relationship vectors;

(4) mapping a two-dimensional plane: using position information of a two-dimensional plane node corresponding to a two-dimensional position of the hyperplane feature map of the patient information model after dimensionality reduction, distinguishing different information categories in the knowledge graph by using colors of the nodes, using a feature importance ranking of a Regularized Gradient Boosted Decision Tree algorithm as the ranking of correlation between each node and disease progression, and using a feature weight value as a calculation weight of a Euclidean distance; and (5) decision making support feedback: taking a domain expert marking result as a standard for the patient information model with an ideal chronic disease management effect, drawing a two-dimensional plane mapping image of the patient data through distributed representation and dimensionality reduction visualization, and calculating the Euclidean distance between geometric centers of various feature areas in the mapping image in combination with the feature weight value to serve as a standardized management target; calculating the Euclidean distance between features of a patient who requires decision making support feedback in the two-dimensional plane mapping image, and comparing the Euclidean distance with a standard numerical value, so as to find a path of similar distance; and obtaining knowledge in the knowledge graph according to distance information of the features;

wherein drawing the hyperplane feature map in step (3) comprises the following sub-steps:

(3.1) encoding triples into spatial distributed vectors by using a translating on hyperplanes (TransH) model, wherein the knowledge in the patient information model is stored in a form of a triple (h, r, t), where h represents a head entity vector, r represents a relationship vector, and t represents a tail entity vector; sets of triples form a directed graph, graph nodes represent entities, edges represent different types of relationships, and the edges are directed to indicate that the relationships are asymmetric; entity distributed vectors of a reflexive relationship, many-to-one, one-to-many and many-to-many relationships are constructed by means of the TransH model, (3.2) optimizing an objective function, wherein for each relationship r in the TransH model, it is assumed that there is a corresponding hyperplane, a relationship projection of r on the hyperplane is expressed as $d_r$, a normal vector of the hyperplane is expressed as $\omega_r$, and $\|\omega_r\|=1$, $h_\perp$ and $t_\perp$ represent projections of h and t on the hyperplane, respectively, then:

$$h_\perp = h - \omega_r^T h \omega_r, \quad t_\perp = t \omega_r$$

defining a scoring function as:

$$f_r(h, t) = \|h_\perp + d_r - t_\perp\|_2^2$$

to obtain the objective function:

$$L = \sum_{(h,r,t) \in S} \sum_{(h',r,t') \in S'} [\varepsilon + f_r(h, t) - f_r(h', t')]_+$$

where, S represents a triple in a knowledge base, S' represents a triple of negative sampling, and ε represents an interval distance parameter with a value greater than 0; and after the training of the TransH model is completed by using a stochastic gradient descent training method, vector representations of the entities and the relationships are obtained;

wherein the step (4) of mapping the two-dimensional plane comprises the following sub-steps:

(4.1) using a t-distributed Stochastic Neighbor Embedding (t-SNE) algorithm to perform dimensionality reduction visualization, wherein:

step i: assuming that a data set X has a total of N data points, and the dimension of each data point $x_i$ is D, reducing the dimensions to two dimensions, that is, expressing all data on the plane;

calculating a conditional probability of similarity between the data points in a high-dimensional space; converting the high-dimensional Euclidean distance between the data points into the conditional probability representative of similarity, wherein the conditional probability $P_{j|i}$ of similarity between high-dimensional data points $x_i$ and $x_j$ is as follows:

$$P_{j|i} = \frac{\exp(-\|x_i - x_j\|^2 / 2\sigma_i^2)}{\sum_{k \neq i} \exp(-\|x_i - x_k\|^2 / 2\sigma_i^2)}$$

where, $\sigma_i$ represents the Gaussian variance centered on the data point $x_i$;

step ii: calculating the conditional probability of similarity between the data points in a low-dimensional space, wherein for low-dimensional corresponding points $y_i$ and $y_j$ of the high-dimensional data points $x_i$ and $x_j$, the conditional probability $Q_{i|j}$ is calculated as follows:

$$Q_{j|i} = \frac{\exp(-\|y_i - y_j\|^2)}{\sum_{k \neq i} \exp(-\|y_i - y_k\|^2)}$$

step iii minimizing a difference in the conditional probabilities, that is, making the conditional probability $Q_{j|i}$ approximate to $P_{j|i}$, it is achieved by minimizing a Kullback-Leibler divergence between the conditional probability distributions, and performing iterative updating by using gradient descent, and a loss function is as follows:

$$C = \sum_i KL(P_i \| Q_i) = \sum_i \sum_j P_{j|i} \log \frac{P_{j|i}}{Q_{j|i}}$$

(4.2) feature importance ranking: using the Regularized Gradient Boosted Decision Tree algorithm to achieve the importance ranking of each entity in the knowledge graph and to obtain the feature weight value, wherein: the data set is a patient information model including samples with known chronic disease management effects or outcomes, each sample contains n-dimensional features; the objective function L of the Regularized Gradient Boosted Decision Tree algorithm includes a loss function and complexity, which are defined as:

$$L = \sum_i l(\hat{y}_i, y_i) + \sum_k \Omega(f_k)$$

$$\Omega(f_k) = \gamma T + \frac{1}{2} \lambda \sum_{j=1}^T \omega_j^2$$

where i represents an $i^{th}$ sample, k represents a $k^{th}$ tree, $\hat{y}_i$ represents a predicted output, $y_i$ represents a label value, T represents a number of leaf nodes, and ω represents a leaf weight value; γ represents a leaf tree penalty regular term, which has a function of pruning; λ represents a leaf weight penalty regular term, which prevents over-fitting; $l(\hat{y}_i, y_i)$ represents a prediction error of the $i^{th}$ sample; $\Sigma_i l(\hat{y}_i, y_i)$ represents the loss function; $\Sigma_k \Omega(f_k)$ represents a complexity function of a tree;

during the growth of the tree, by comparing the values of the objective function before and after splitting, the splitting with a minimum value of the objective function after the splitting is an optimal splitting point:

$$\text{Gain} = \frac{1}{2} \left[ \frac{G_L^2}{H_L + \delta} + \frac{G_R^2}{H_R + \delta} - \frac{(G_L + G_R)^2}{H_L + H_R + \delta} \right] - \delta$$

where δ represents a complexity cost introduced by adding a new leaf node, $G_L$ represents a left sub-tree gradient value, and $H_L$ represents a second derivative of a left sub-tree sample set; $G_R$ represents a right sub-tree gradient value, and $H_R$ represents a second derivative of a right sub-tree sample set; if Gain<O, then the new leaf node will not be split; and a feature importance score is realized by calculating a total gain brought by a certain feature in all trees every time when the node is split; and the corresponding feature weight value is obtained by calling a get_score method of a booster parameter.

2. The patient data visualization method for assisting decision making in chronic diseases according to claim 1, wherein knowledge content of the knowledge graph covers disease diagnosis, inspection items, physical sign states, related diseases, therapeutic drugs, living habits, measurement units, and detection quantities.

3. The patient data visualization method for assisting decision making in chronic diseases according to claim 1, wherein the patient data collected in step (2) comprises patient health data manually input in a daily mobile terminal or collected by a wearable device, and patient electronic medical record data recorded by a regional chronic disease management center.

4. The patient data visualization method for assisting decision making in chronic diseases according to claim 1, wherein during an RDF conversion process of the patient data in step (2), the patient data in a relational database are mapped into an RDF format by using the D2R semantic mapping technology; the D2R semantic mapping technology defining mapping rules for converting the patient data in the relational database into the RDF format and completing data mapping, which refers to mapping tables and fields in the relational database into categories and attributes in an OWL file respectively, and obtaining a relationship between the categories from a table that expresses the relationship.

5. The patient data visualization method for assisting decision making in chronic diseases according to claim 1, wherein in step (5), the knowledge in the knowledge graph is obtained according to the distance information of the features by using a SPARQL Protocol and RDF Query Language (SPARQL) query language and Jena rule reasoning, so as to generate a personalized management plan for a patient.

6. The patient data visualization method for assisting decision making in chronic diseases according to claim 5, wherein in step (5), a SPARQL query statement comprises conditions to which query information and names should conform, the conditions appear in a form of triples and are arranged in an order of <subject, predicate, object>, that is, subject, predicate, and object, and a query result is actually a matching result of condition triples and RDF triples in a data file.

7. The patient data visualization method for assisting decision making in chronic diseases according to claim 1, wherein during the feature importance ranking process in step (4), the Regularized Gradient Boosted Decision Tree algorithm parameter training is performed by using a grid search method, comprising a general parameter, an improving parameter, and a learning target parameter; and the general parameter controls macro parameters, the improving parameter controls improvement in each step, and the learning target parameter controls performances of a training target.

* * * * *